United States Patent
Matsumura et al.

(10) Patent No.: US 6,801,913 B2
(45) Date of Patent: Oct. 5, 2004

(54) MEDICAL INSTRUMENT CONTROL SYSTEM

(75) Inventors: Isao Matsumura, Kanagawa (JP); Yoshito Yoneyama, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 528 days.

(21) Appl. No.: 09/978,212

(22) Filed: Oct. 17, 2001

(65) Prior Publication Data

US 2002/0059257 A1 May 16, 2002

(30) Foreign Application Priority Data

| Oct. 20, 2000 | (JP) | ........................... 2000-321488 |
| Oct. 20, 2000 | (JP) | ........................... 2000-321489 |
| Oct. 20, 2000 | (JP) | ........................... 2000-321490 |
| Oct. 20, 2000 | (JP) | ........................... 2000-321491 |

(51) Int. Cl.$^7$ .......................................... G06F 17/30
(52) U.S. Cl. ............................. 707/10; 707/7; 707/3; 707/4; 707/5
(58) Field of Search .................... 707/7–10, 100–104.1, 707/200–205; 705/1–3, 7–8, 22–25, 28–29, 404–411; 257/25.019, 25.029, 25.032; 348/61, 65, 76, 66; 600/101, 109, 112, 104, 108, 110, 160, 169; 606/1–10, 113, 151, 205, 207, 167, 27–29; 604/19; 219/200, 221, 227; 623/4.1, 611–612

(56) References Cited

U.S. PATENT DOCUMENTS

| 4,657,356 A | 4/1987 | Matsumura .................. 359/377 |
| 4,678,297 A | 7/1987 | Ishikawa et al. ............. 351/208 |
| 4,690,525 A | 9/1987 | Kobayashi et al. .......... 351/206 |
| 4,699,481 A | 10/1987 | Matsumura .................. 351/205 |
| 4,762,410 A | 8/1988 | Sekiguchi et al. ........... 351/206 |
| 4,813,778 A | 3/1989 | Madate et al. ............... 351/208 |
| 4,867,554 A | 9/1989 | Matsumura .................. 351/205 |
| 4,917,458 A | 4/1990 | Matsumura .................. 351/212 |
| 4,991,584 A | 2/1991 | Kobayashi et al. .......... 600/401 |
| 4,999,009 A | 3/1991 | Matsumura .................. 351/212 |
| 5,018,851 A | 5/1991 | Matsumura .................. 351/214 |
| 5,037,194 A | 8/1991 | Kohayakawa et al. ....... 351/224 |
| 5,056,522 A | 10/1991 | Matsumura et al. ......... 600/405 |
| 5,374,813 A | * 12/1994 | Shipp ........................... 235/375 |
| 5,659,741 A | * 8/1997 | Eberhardt ................. 707/104.1 |
| 5,675,744 A | * 10/1997 | Tsujii ............................. 705/3 |
| 5,781,442 A | * 7/1998 | Engleson et al. ............ 700/214 |
| 6,018,713 A | * 1/2000 | Coli et al. ...................... 705/2 |
| 6,255,951 B1 | * 7/2001 | De La Huerga .......... 340/573.1 |
| 6,611,846 B1 | * 8/2003 | Stoodley ................... 707/104.1 |
| 6,694,167 B1 | * 2/2004 | Ferre et al. .................. 600/424 |

OTHER PUBLICATIONS

"J. Retzlaff, Lens Implant Power Calculation—A Manual for Ophthalmologist & biometrists", 3$^{rd}$ Ed., Slack, Inc., Thorofare, NJ, 1990, pp. 1–58.

* cited by examiner

Primary Examiner—Greta Robinson
Assistant Examiner—Linh Black
(74) Attorney, Agent, or Firm—Fitzpatrick, Cella, Harper & Scinto

(57) ABSTRACT

A medical-instrument service providing system receives an online order for a medical instrument via a communication network from a service utilizing terminal of a medical institution, accesses a stock control server controlled by a supplier of the medical instrument, to check whether or not the on-order medical instrument is in stock in the supplier. If the on-order medical instrument is in stock in the supplier, the system instructs to deliver the medical instrument to the medical institution. If the on-order medical instrument is insufficient in stock, the system accesses a stock control server, controlled by other institution than the medical instrument, to check whether or not the instrument is in stock, via the communication network. If the on-order medical instrument is in stock, the system instructs to supply the medical instrument to the medical institution from the other institution.

43 Claims, 10 Drawing Sheets

FIG. 5

INPUT PATIENT INFORMATION.

| | |
|---|---|
| PATIENT ID | NAKED VISION |
| KERATOMETRIC VALUE | CORRECTED VISUAL ACUITY |
| AXIAL LENGTH | SPHERICAL POWER |
| POST-SURGERY REFRACTION VALUE | CYLINDER (POWER) |
| CORNEAL DIAMETER | CYLINDER AXIS |
| PUPIL DIAMETER | TYPE ○ CAT ● PHAKIC |
| | INSERTION POSITION ● ANTERIOR CHAMBER ○ POSTERIOR CHAMBER |

[ SEARCH APPROPRIATE LENS ]    [ CUSTOMIZE PARAMETER ]

FIG. 6

SEARCH RESULT

| MAKER | MODEL | POWER | STOCK |
|---|---|---|---|
| A | AP-410NV | +15.0D | ● |
| A | U458B | +15.5D | ● |
| A | SI-84F | +14.5D | |
| B | MB-45BC | +15.0D | |
| B | UV-30NA | +14.5D | |

ONLINE ORDERING   RE-SEARCH

F I G. 8

CHECK ORDER INFORMATION

| MAKER | MODEL | POWER | VOLUME | HOSPITAL STOCK | MAKER STOCK |
|---|---|---|---|---|---|
| A | AP-410NV | +24.0D | 2 | ● | ● |
|  |  | +24.5D | 1 | ● | ● |
|  |  | +25.0D | 1 | ○ | ● |
|  |  |  |  |  |  |
|  |  |  |  |  |  |

ORDER    CANCEL

FIG. 9

```
                    ELECTRONIC MEDICAL RECORD

ID :        NAME :         AGE :    (MALE/FEMALE) BIRTHDAY :

DATE :

┌─────────────────────────────┐  ┌──────────────────────────┐
   │  PATIENT'S PROFILE          │  │ RESPONSIBLE DOCTOR :     │
   │                             │  ├──────────────────────────┤
   │                             │  │ INITIAL CONSULTATION     │
   │                             │  │                          │
   │                             │  │                          │
   ├─────────────────────────────┤  │                          │
   │ ANAMNESIS : ·———   ·———    │  │                          │
   │             ·———   ·———    │  │                          │
   │             ·———     · OTHER│  │                          │
   ├─────────────────────────────┤  └──────────────────────────┘
   │ DIAGNOSIS :                 │
   │                             │  ┌──────────────────────────┐
   └─────────────────────────────┘  │ TREATMENT :              │
                                    │                          │
   ┌──────────────┐ DATE :          │                          │
   │EXAMINATION DATA│ ───────        │                          │
   └──────────────┘                  │                          │
   NAKED                             │                          │
   VISION :       REFRACTION :       │                          │
   CORRECTED      KERATOMETRIC       │                          │
   VISUAL ACUITY :         VALUE :   │                          │
   AXIAL         ( MEASURING    )    │                          │
   LENGTH :      (  DEVICE :    )    │                          │
                                     └──────────────────────────┘
   ┌──────────┐   ┌──────────┐       ┌──────────────────────────┐
   │  METHOD  │   │   IOL    │       │ FINDINGS :               │
   └──────────┘   └──────────┘       │                          │
    ·———           ·———              │                          │
    ·———           ·———              │                          │
    ·———           ·———              │                          │
    ·———           ·———              │                          │
    · OTHER        · OTHER           │                          │
                                     └──────────────────────────┘
```

OVERVIEW OF PRODUCT PACKAGE

MEDICAL INSTRUMENT CONTROL SYSTEM

FIELD OF THE INVENTION

The present invention relates to a system including medical institutions such as a hospital and a medical laboratory and a supplier to supply a medical instrument to these medical institutions.

More particularly, the present invention relates to a method of supplying a medical instrument to medical institutions such as hospitals and medical laboratories and a system to check a stock status of the medical instrument.

Further, the present invention relates to a service providing method and service providing system to support selection of medical instrument for medical institutions such as hospitals and medical laboratories.

Further, the present invention relates to an electronic medical recording system and a medical foolproof system utilized in medical institutions such as hospitals and medical laboratories.

Further, the present invention relates to a medical instrument control method and control system for controlling a medical instrument used in the medical institutions such as hospitals and medical laboratories.

BACKGROUND OF THE INVENTION

In medical institutions such as hospitals and medical laboratories, various medical instruments are used in surgery and medical inspections. The medical instruments are e.g. tools, medicine, and implanted devices including implanted tools (devices surgically placed in the body such as an intraocular lens, a pacemaker and artificial organs). Further, the medical institutions use these various instruments supplied from suppliers such as makers. Some of the instruments are stocked in the medical institutions, and otherwise, orders for some instruments are placed with the suppliers when required.

However, in the medical institutions, it is very troublesome to control stocks of the medical instruments because timing of use cannot be predicted without difficulty, and various types of instruments are used. Generally, patients fall ill unexpectedly and demands cannot be predicted without difficulty, and calculated control cannot be performed. On the other hand, in the scene of medical service, emergent surgery and inspections may be frequently performed. Accordingly, it is a very serious object to construct a system to quickly supply medical instruments. This is a specific problem to the field of medical treatment.

Especially, a part of implanted tools and medicine are degraded with time, and they are not appropriate for long-term storage. As the medical institutions cannot hold such instruments for a long period, they repeat ordering in accordance with necessity. That is, a high frequency of ordering must be made. Further, the makers must predict demands and control manufacturing and quick supply of products so as to cover every possible situations.

As an example of implanted tool which is degraded with time, an intraocular lens (including an intraocular contact lens) used in ophthalmologic surgery is known. A hospital selects a lens appropriate to a patient's eye and uses it in the surgery. However, intraocular lenses have various sizes and shapes corresponding to individuality of patients, and a lens necessary for surgery is not always stocked in the hospital. Further, if the patient's eye has an extraordinary size and/or shape, an appropriate intraocular lens may be out of stock even in the lens maker. However, in emergency ophthalmologic surgery, the supply of lens must not be delayed.

Further, the medical institutions have another problem. That is, the selection of implanted tool appropriate to a patient greatly depends on a responsible doctor's expert knowledge and experience, i.e., so-called know-how. In the case of intraocular lens, a doctor of the hospital performs ophthalmologic measurement and diagnosis on the patient, and selects an intraocular lens having optimum size and shape for the patient based on the results of measurement. Several mathematically-expressed selection criteria for calculation of lens power are known. However, in some cases, the coefficient used in the calculation may be changed in accordance with the type of intraocular lens (difference in makers etc.). The coefficient, corresponding to the above know-how of each doctor, may cause a difference in type of finally-selected intraocular lens in accordance with a numerical value determined by the doctor. That is, how to improve the selection criteria to a higher level and attain homogeneity is a significant problem.

Further, in the medical institutions, by virtue of the development of recent information technology, electronization of patients' medical records is expected. In conventional patients' medical records, personal data, medical measured values and the like are written, however, in electronic medical records, more input items can be realized and detailed information on medical products used for respective patients can be recorded. As to surgically used tools such as implanted tools, to prevent omission of input or input error to the electronic medical record, it is desirable to input product information to the record on the spot of surgery. Accordingly, one of the problems is how to realize the on-the-spot input for prevention of omission of input or input error.

In the case of intraocular lens as an example of implanted tool, as described above, one intraocular lens appropriate to a patient's eye is selected from various types of intraocular lenses. There may be no problem if a doctor who selects a lens and a doctor who surgically place the selected lens in the patient's eye are the same person; otherwise, the record of lens made by the doctor who selected the lens is the only information of intraocular lens to be surgically placed in the patient's eye. Accordingly, to perform the safest surgery, a foolproof system is desired to finally check an intraocular lens to be used in surgery before the surgery, and how to realize the system is a further problem.

SUMMARY OF THE INVENTION

The present invention has been made in consideration of the above problems specific to the medical field, and has its object to solve the problems related to supply of medical instruments, i.e., demands cannot be predicted without difficulty, and further, the instruments must be quickly supplied, by constructing novel method and system.

A more particular object of the present invention is to provide method and system for online ordering for a medical instrument by utilizing a communication network in a timely and economical manner.

Another object of the present invention is to provide method and system for online ordering for a medical instrument appropriate to a patient in a simple manner by utilizing a communication network.

Further, another object of the present invention is to provide method and system for efficient delivery and manufacturing control for a maker of medical instrument by utilizing a communication network.

Further, another object of the present invention is to provide method and system for providing an excellent after-sales service regarding a medical instrument by utilizing a communication network.

Further, another object of the present invention is to provide method and system for reduction of shortage of medical instruments by utilizing a communication network.

Further, another object of the present invention is to provide method and system of service for supporting medical institutions to select a medical instrument appropriate for a patient by utilizing a communication network.

Further, another object of the present invention is to provide method and system for providing a service to support selection of medical instrument, with a selection criterion which is advanced in accordance with increment in number of use of service.

Further, another object of the present invention is to provide method and system to foster timely development and improvement of medical products and after-sales support service by utilizing a communication network.

Further, another object of the present invention is to solve the above problems related to use of medical instruments in medical institutions by constructing a novel system.

More particularly, one of the objects of the present invention is to provide an electronic medical recording system for medical services to cover every possible situations for each patient.

Further, another object of the present invention is to provide a foolproof system upon use of medical instrument to a patient and a terminal apparatus to realize the system.

Other features and advantages of the present invention will be apparent from the following description taken in conjunction with the accompanying drawings, in which like reference characters designate the same name or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

FIG. 5 is an example of screen image for inputting patient data;

FIG. 6 is an example of screen image showing a list of search result;

FIG. 8 is an example of screen image for checking online ordering;

FIG. 9 is an example of screen image of electronic medical record; and

DETAILED DESCRIPTION OF THE PREFERRED EMBODIMENTS

Preferred embodiments of the present invention will now be described in detail in accordance with the accompanying drawings.

In the following description, as an example of medical instrument, an intraocular lens (IOL) placed in a patient's eye will be used. The IOL is an example of an implanted tool placed in a patient's body. However, the present invention is not limited to the intraocular lens but is applicable to other implanted tools (a pacemaker, artificial organs, dental implants, artificial bones and the like to be placed in the body). Further, the present invention is applicable to medical instruments selected for respective patients such as specialized instruments used in surgery using the above implanted tools, medicine, consumables used in examinations and treatments, and the like.

Figure 1:
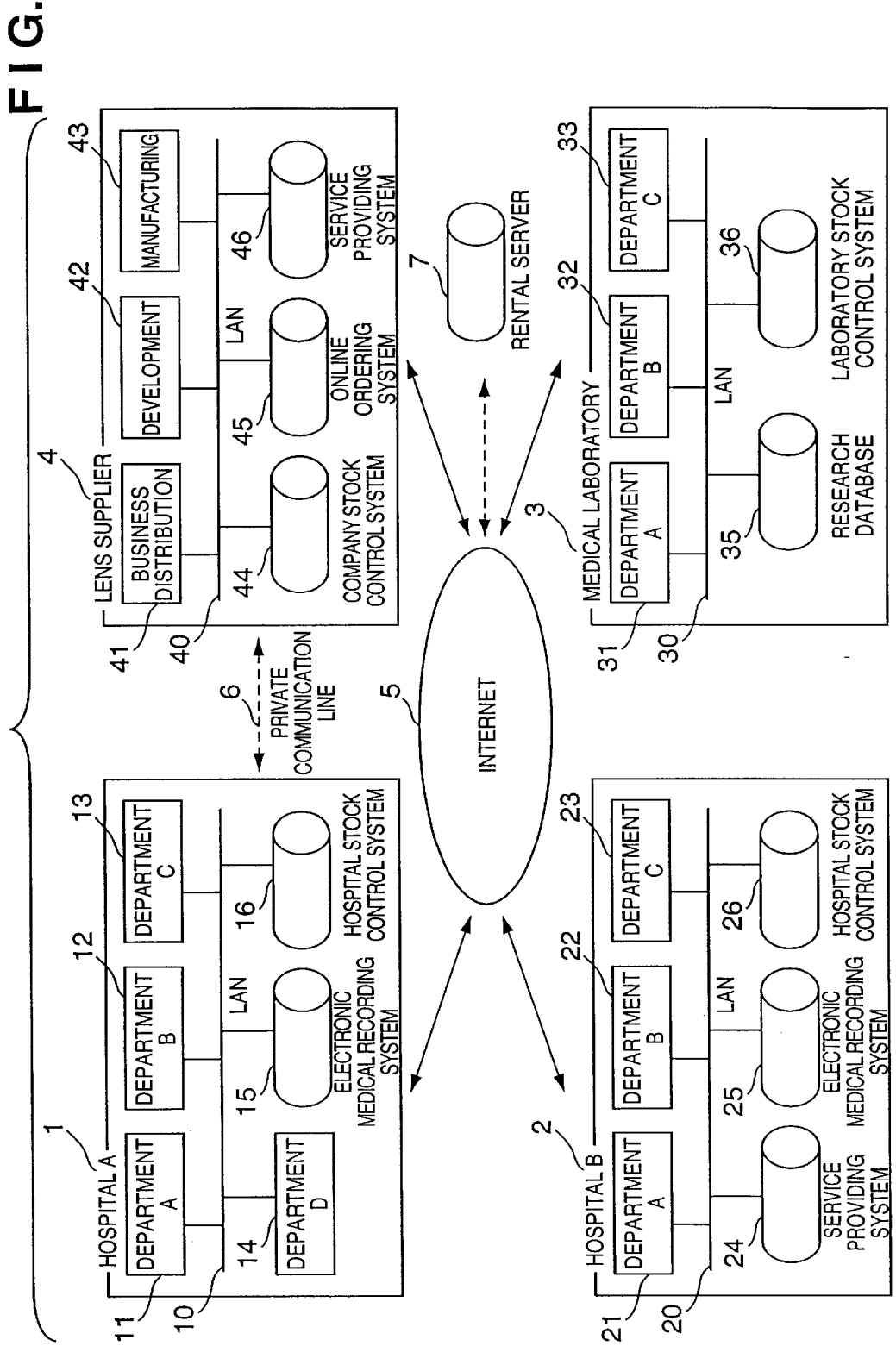
FIG. 1 is a block diagram showing a hardware network construction of service system.

FIG. 1 is a block diagram showing the entire construction of information communication network including medical institutions such as a hospital and a medical laboratory and a supplier (company organization having a manufacturing department, a business department, a distribution department, a distribution department and the like) of medical instrument used in the medical institutions. In FIG. 1, a hospital A (1), a hospital B (2), a medical laboratory (3) and a lens supplier (4) (medical instrument supplier) are interconnected via the Internet (5).

In the hospital A (1), a hospital LAN (Local Area Network) (10) is constructed, and computer devices and medical measuring devices held in respective clinical departments, a department A (11), a department B (12), a department C (13) and a department D (14), are interconnected via the LAN. If the hospital A is a general hospital, the hospital has departments of various fields. For example, in the field of ophthalmology, various medical measuring devices such as a refractometer for measurement of refraction, a keratometer (ophthalmometer) for measurement of corneal power, an ultrasonic haploscope for measurement of axial length, a visuscope for measurement of visual acuity, a digital retinal camera for obtaining a fundus image, a velocimeter for blood velocity measurement of retinal bloodflow, a perimeter for measurement of visual field, tonometer for measurement of ocular pressure, and the like, are used.

The hospital LAN (10) is connected to an electronic medical recording system (15) and a hospital stock control system (16). The electronic medical recording system (15) has a server which includes a database for control of all the electronized patient information handled in the respective departments and which is accessible from the respective departments in client/server form. More particularly, the patient information includes patient identification data (ID code, name and the like), examination and treatment records (date, contents of examination, examination data, doctor's findings, contents of treatment, medical instruments) and the like. The medical instruments are instruments, medicine, tools attached/placed to/in the body including implanted tools, and the like. FIG. 9 is an example of user interface for electronic medical recording. The above-described patient information is displayed.

The hospital stock control system (16) has a server including a database for control of stocked medical instruments used in the hospital. The stock control system controls the medical instruments by product serial code. The hospital stock control system (16) is accessible from the respective clinical departments and stock control department of the hospital in client/server form. Further, as described later, the medical instrument supplier is permitted, on some conditions, to access the hospital stock control system (16) via an external network (in the present embodiment, the supplier can access only data related to stock statuses of products of the supplier). A doctor or assistant to perform treatment can check whether or not medical instrument(s)

necessary for the treatment or examination are stocked in the hospital by accessing the hospital stock control system (16) from an access terminal (PC or workstation) of the department.

Similarly, in the hospital B (2) different from the hospital A (1), a department A (21), a department B (22), a department C (23), an electronic medical recording system (25), a hospital stock control system (26) and the like are interconnected as a network via a hospital LAN (20). The details of the electronic medical recording system (25) and the hospital stock control system (26) are the same as those in the case of the hospital A (1). The difference from the hospital A (1) is that the hospital LAN (20) of the hospital B (2) is connected to a further local service providing system 24. As described later, the service providing system 24 includes a server to provide a selection support service to select an appropriate medical instrument from patient information, and the server is accessible from the respective departments of the hospital B in client/server form.

Further, in the medical laboratory (3) different from the hospital A (1) and the hospital B (2), a department A (31), a department B (32) and a department C (33) are interconnected as a network via a laboratory LAN 30. The LAN is connected to a stock control system (35) and a database system (34) holding research data, and accessible from the respective departments in client/server form.

The lens supplier (4) is given as an example of medical instrument supplier. In this embodiment, it is a supplier of intraocular lens for medical surgery as example of implanted tool. The supplier may be any type of company as long as it is within the scope of the present invention. For example, the supplier may be any of other companies which supply other implanted tools (a pacemaker, artificial organs, dental implants, artificial bones and the like), medicine, consumables used in examinations and treatment, and the like. In the lens supplier (4), a business distribution department (41) (including sales and distribution sections), a development department (42) and a manufacturing department (43) are interconnected as a network via a company LAN (40). The network is connected to a company stock control system (44), an online ordering system (45), and a service providing system (46) for supporting lens-selection and the like. The company stock control system (44) has a server including a database for controlling stock statuses of all the products handled by the lens supplier. The online ordering system (45) has a server to receive online orders for products from the medical institutions (1, 2 and 3) as customers via the Internet (5).

The service providing system (46) has a server to provide a service to support selection of lens in correspondence with a patient by the above customer, and provides an online service in client/server form. The particular services will be described later. The online ordering system (45) and the service providing system (46) respectively have hardware constituents including a storage device (hard disk or memory) holding a computer program defining a procedure of the service and data group of the database, a processor (computation device) for execution of the program, and a network interface for connection with the LAN.

Note that instead of execution of program of all the service functions by the processor on the server side, a program defining a part or all of the functions of the service (, and data of the database if necessary,) may be held on the client (service utilizing terminal) side for execution of the function(s) by the processor on the client side. In this case, the program executed on the client side may be transferred via the network from the server to the client, or may be previously installed as software to use the service in the storage device of the client. For the sake of quick service update, it is preferable to download the program in form of applet from the server to the client via the network upon every use of the service and execute the program on the client side.

The LANs of the hospital A (1), the hospital B (2), the medical laboratory (3) and the lens supplier (4) are connected to the Internet (5) via a gateway (not shown) including a firewall. For protection of privacy of patients and the hospitals, a high level security function is necessary for use of the Internet allowing use of public line. For this purpose, a security system using encrypted data communication and user ID and password is employed. To completely exclude possibility of third person's intrusion, a private communication line (6) may be used without the Internet for data communication between the lens supplier (4) and the hospital (1). Further, the respective servers (46 and 45) to provide the online ordering service and the lens-selection support service controlled by the lens supplier (4) may be placed, not on the LAN (40) in the lens supplier (4) but on a rental server (7) provided on the Internet by a third person. In this case, the lens supplier (4) performs program correction and data transfer via the Internet (5), thus remotely controls the contents of the rental server (7).

The hardware network construction is as described above. Next, particular contents and procedures of the service will be described.

Figure 2:
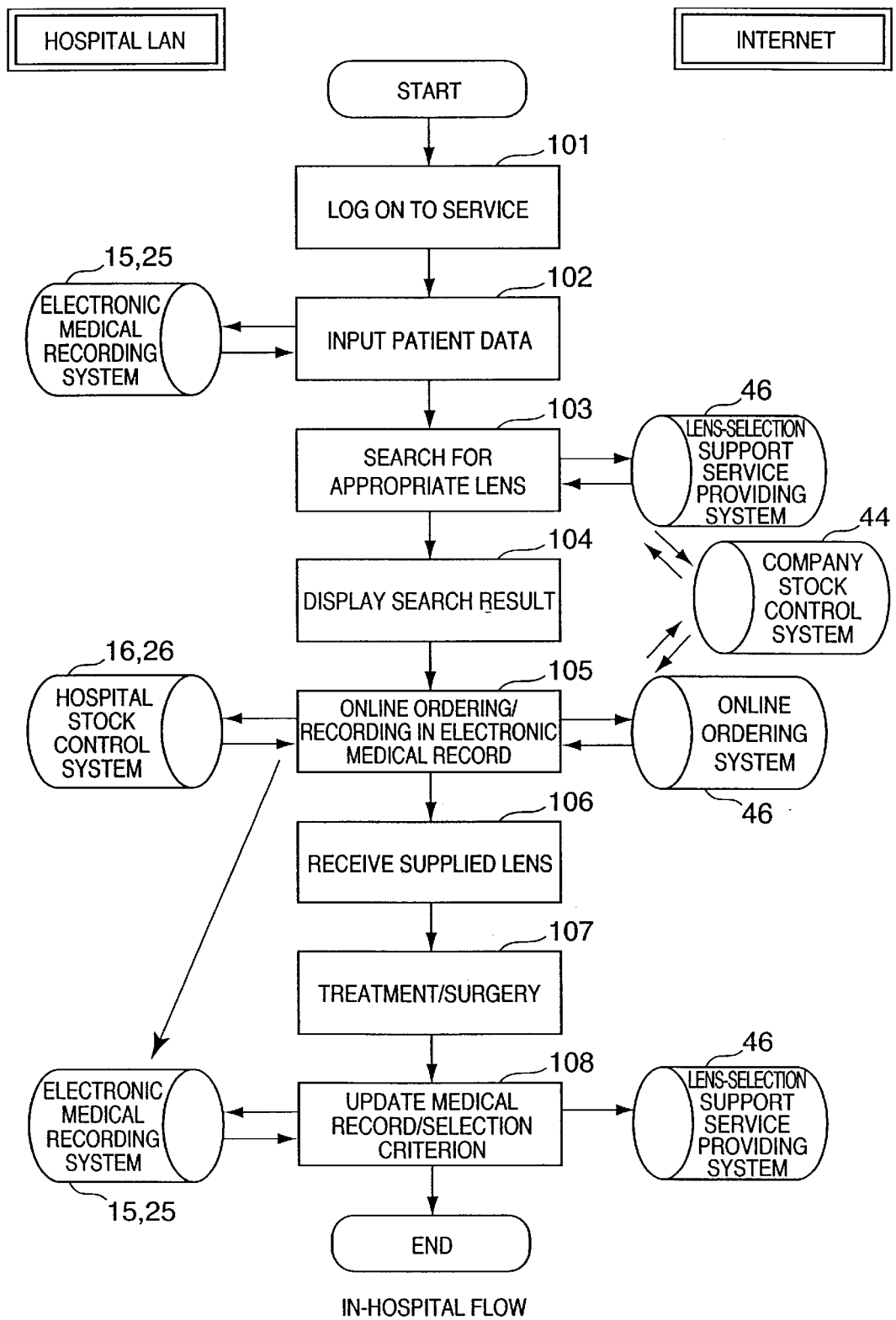
FIG. 2 is a flowchart showing a procedure in a medical institution.

FIG. 2 is a flowchart showing a standard procedure in the medical institution (the hospital A, the hospital B or the medical laboratory) utilizing the present service system. Since the intraocular lens has various sizes and shapes corresponding to individuality of patients, a doctor or examination technician, or assistant in the respective departments is to perform an operation to select an intraocular lens appropriate to a patient. The lens supplier provides the lens-selection support service for selecting a lens appropriate to a patient by utilizing various information related to lenses owned by the company.

Figure 4:
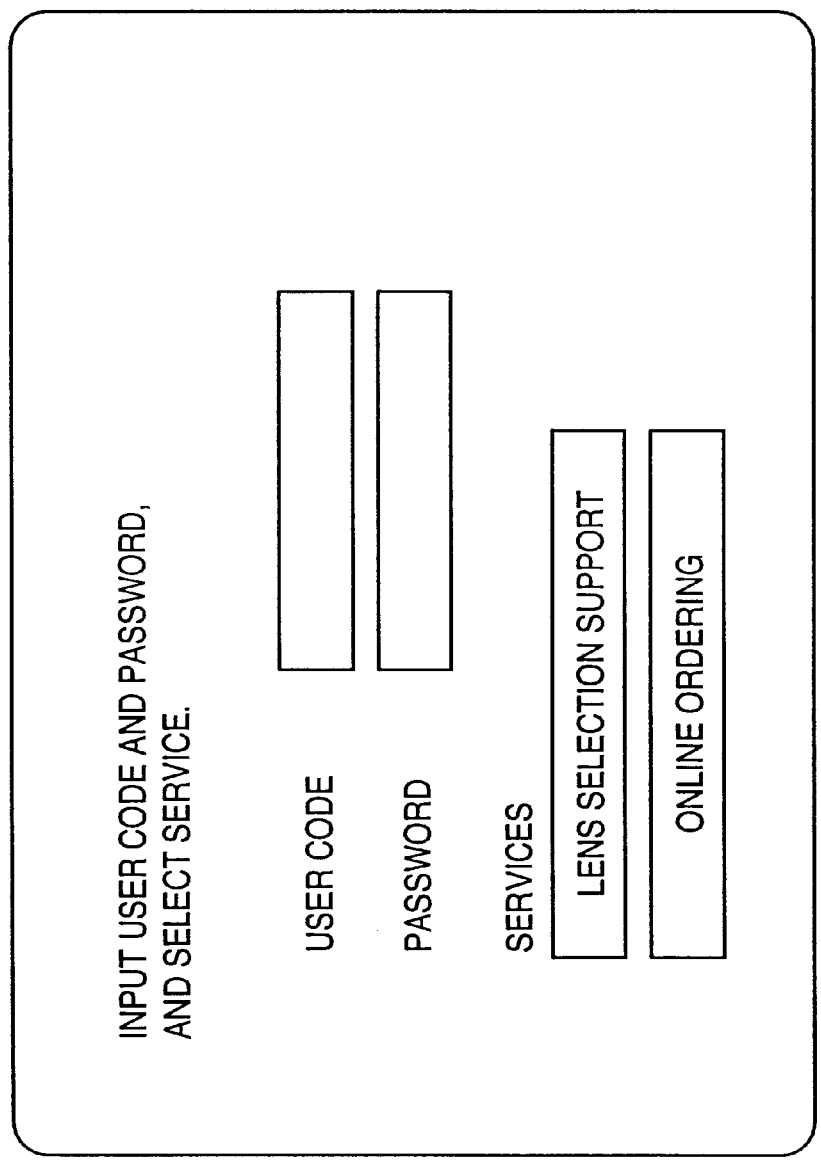
FIG. 4 is an example of screen image for service selection.

In FIG. 2, at step 101 (log on to service), a doctor or examination technician or assistant in the respective departments of the medical institution accesses the service providing server of desired lens supplier via the LAN and the Internet from the service utilizing terminal (PC or workstation connected to the network). At this time, user code and password provided to the service user are inputted, and a button of desired service is depressed. Only a registered user (the hospital A or staff of the hospital) can log on to the service. As shown in FIG. 4, service selection buttons are "lens selection support" and "online ordering".

Step 102 (input patient data) and the subsequent steps are procedure steps performed when the lens selection support service has been selected. Patient information of a patient to take surgery for placement of intraocular lens is inputted. FIG. 5 is an input screen image displayed on the service utilizing terminal. If the "lens selection support" button as shown in FIG. 4 is clicked by a mouse of the service utilizing terminal, the screen image as shown in FIG. 5 is displayed. Input data items are a patient ID, a keratometric value (corneal refraction) measured by a keratometer (refractometer), an optic axis length measured by a ultrasonic haploscope, a post-surgery refraction of the patient's eye after insertion of the intraocular lens, a corneal diameter, a pupil diameter, naked eye sight, corrected eye sight, a spherical angle upon correction, astigmatism refraction and an astigmatism axial angle. Further, there are selection items of intraocular lens type (CAT or PHAKIC) and insertion position (anterior chamber or posterior chamber). These data are automatically read from the patient's electronic record through the hospital LAN and displayed on the screen.

The data reading from the electronic medical record is made by a hospital network access program installed in the service utilizing terminal. An item with no data from the electronic medical record is displayed as blank, and the doctor inputs a numerical value from a keyboard of the service utilizing terminal in accordance with necessity. Further, if the doctor desires, a numerical value of the input item, read from the electronic medical record, can be rewritten with a different numerical value. An execution button of "search appropriate lens" is displayed in a lower part of the screen image, and if this button is clicked by the mouse, the process moves to the next step 103. Further, for the user's customizing a parameter as lens selection criterion, a "customize parameter" button is displayed.

At step 103 (search for appropriate lens), the lens-selection support service providing system 46 searches for an appropriate intraocular lens in accordance with the patient data received via the Internet and a predetermined selection criterion. The procedure of the lens search is as described bellow.

First, a lens power appropriate to the patient's eye is calculated by utilizing a lens power formula for selecting a lens power which is well known in the field of ophthalmology. SRK/T formula is one of the lens power formulas. The details of the expression is described in John A. Retzlaff, MD et al.: "LENS OMPLANT POWER CALCULATION (Third Edition), SLACK Incorporated. Further, other various lens power formulas such as the Binkhorst formula, the Colenbrander-Hoffer formula and the Regression formula than the SRK/T formula may be used in place of the SRK/T calculation.

Parameters used in the SRK/T calculation include a parameter called A constant specific to an intraocular lens type, and other parameters such as anterior chamber depth. In some cases, these parameters should be slightly varied in accordance with intraocular lens maker. Generally, the lens supplier provides recommended parameter values, however, in some cases, the numerical values are varied by respective doctors' decision, which corresponds to so-called doctor's know-how.

In the present embodiment, when the user depresses the "customize parameter" button, an input item for inputting a numerical value of the above-described A constant, different from the maker's recommended value, is displayed, and the user inputs a numerical value and calculates a lens power. The value of the A constant used in the lens selection calculation is automatically recorded in the lens-selection support service providing system 46 of the lens supplier. As described later, the recommended A constant value is obtained by averaging values from many users. Generally, this value is used in lens power calculation.

The lens-selection support service providing system 46 obtains the lens power by the above formula, then searches the database with the obtained value as a search condition, and further with other patient data such as the corneal diameter data and the pupil diameter data as other search conditions, for lenses satisfying all the search conditions. That is, from the various types of intraocular lenses stored in the database, lenses satisfied "the lens type having the calculated lens power (condition 1)" and "the lens appropriate to the patient's corneal diameter data and pupil diameter data and the like (condition 2)" are extracted. As a result of search, all the models of intraocular lenses having corresponding power and lens diameter specification are selected. In the present embodiment, as the database of the lens-selection support service providing system includes data on various models of intraocular lenses by plural makers as well as data on 1 maker (the supplier itself), a search for an appropriate intraocular lens can be made regardless of maker.

At step 104 (display search result), the result of the above search is displayed in list form on the service utilizing terminal. FIG. 6 is an example of the search result displayed on the display screen of the service utilizing terminal. In this example, lenses by different makers satisfying the search conditions are displayed in the list, however, it may be arranged such that only models of specific 1 maker (the supplier itself) are displayed. Further, stock statuses, i.e., whether or not the selected intraocular lenses are in stock, are displayed. The stocks are checked by accessing the company stock control system (44) from the service providing system (46) via the company LAN (40) (via the Internet in use of rental server). The doctor finally determines a lens based on the search result. Then the doctor opens the patient's electronic medical record, and inputs the model, the power, a predicted refraction value after insertion, the features of the selected lens and the like, into the electronic medical record.

Note that if the doctor cannot find an appropriate lens from the search result, as the process returns to the patient data input image in FIG. 5 by depression of "re-search" button in FIG. 6, the doctor can slightly vary the patient data values or selection parameters and make another search. Further, if the patient's eye is extraordinary and any of standardized lenses cannot be used, an order can be placed for a customized lens to be manufactured in a factory.

At step 105 (online ordering), an online service to receive an order for an intraocular lens is provided. This service operates in cooperation with the online ordering service system (45) of the lens supplier on the initiative of the local server of the hospital. The service user is not conscious of the position of the server.

Figure 7:
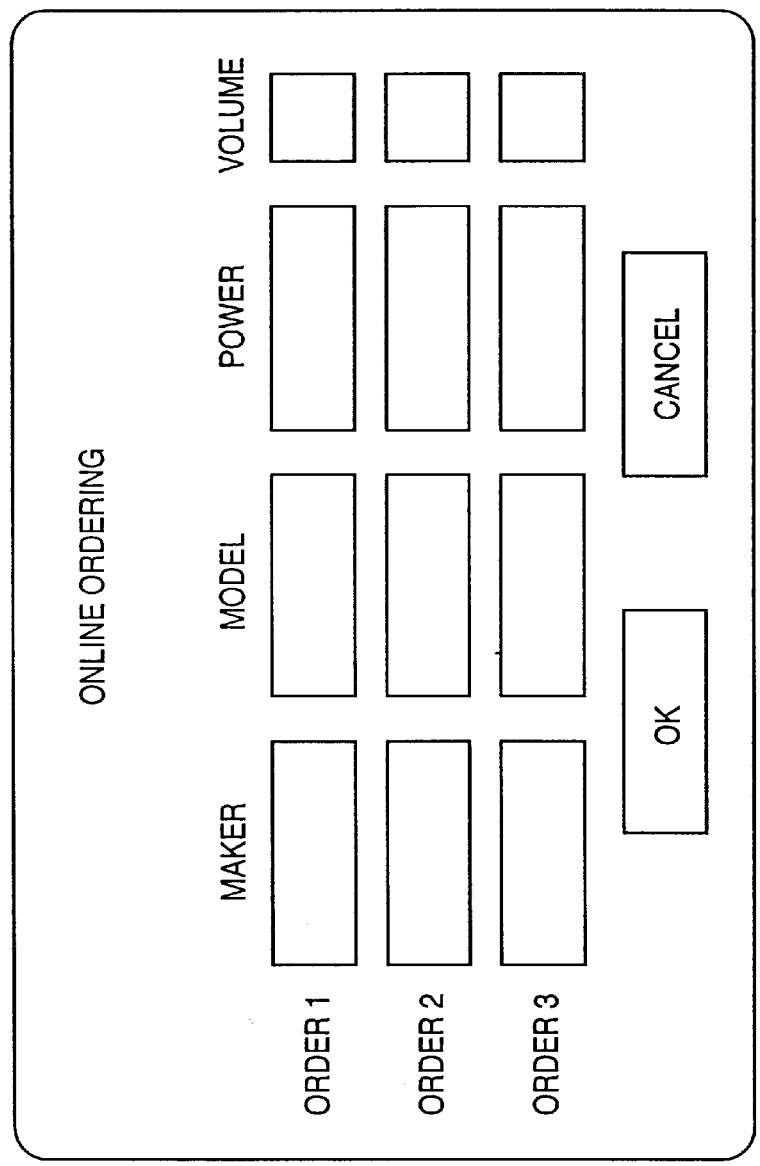
FIG. 7 is an example of screen image of online new ordering.

In a case where an online order is made immediately after the search by the lens-selection support service, the "online ordering" button is depressed in the screen image in FIG. 6 showing the search result. Then the screen changes to an online ordering image as shown in FIG. 7. In the screen image, 4 input items of maker, a model name, a power and the volume of on-order lens are displayed, and plural orders (order 1, order 2, order 3, . . . ) can be made. At normal times, the results of search by the lens-selection support service is automatically inputted into the respective items and displayed. Then the user deletes unnecessary items leaving necessary ones, thereby designates on-order lens(es). After the designation, when an "OK" button in a lower position of the screen image is clicked, the screen changes to an order check image as shown in FIG. 8. Note that if the "online ordering" is selected in the service selection at the initial step 101 (FIG. 4), the screen directly changes to an ordering image in FIG. 7 for placement of new order. In the case of new order, as input items are blank, desired name and numerical values are inputted into one or plural fields of the maker, the model name, and the power, then a desired number is inputted into the item of volume of on-order lens (in use of pull-down menu for selection, the operability can be improved), and an "OK" button is depressed. Then models corresponding to the conditions are displayed in list as shown in FIG. 8.

FIG. 8 is an example of screen image to finally check an online order displayed on the service utilizing terminal. The stock statuses of the respective intraocular lenses in the hospital, and stock statuses of the lenses in the maker are automatically checked and check results are displayed on the right side of the screen. It may be arranged such that numerical values indicating the number of stocked items instead of stock statuses are displayed. The data on the stock in the hospital is provided from the hospital stock control system (16, 26, 35), and the data on the maker stocks is provided from the maker stock control server 44. The service user checks the displayed contents and clicks "order", and the order is completed. Upon completion of order, as the intraocular lens used in treatment of the patient's eye is determined, the information of the lens is inputted in the electronic medical record. Note that if "cancel" is clicked, the order is cancelled. Furthermore, it is also possible to order other medical instruments to secure the stock. Such an order does not synchronize with the medical record.

Regarding the intraocular lens on order by the online ordering, process differs in accordance with its stock status in the hospital. If the lens is stocked in the hospital, the on-order lens, the orderer and the orderer department and the like are recorded in the hospital stock control system, and the stock control department of the hospital delivers the intraocular lens in accordance with the place and time of the surgery. If the lens is insufficient in stock, an order is automatically placed with the online ordering system (45) of the lens supplier via the Internet.

At step 106 (receive supplied lens), if the lens is stocked in the hospital, the on-order lens is delivered to the doctor to perform the surgery from the stock control department of the hospital immediately or at necessary timing. Further, if an order has been placed with the external supplier, the on-order lens is supplied from the business department or distribution department of the lens supplier to the stock control department of the hospital, then the serial number of the product is registered in the hospital stock control system, and the lens is delivered to the doctor at necessary timing.

At step 107 (treatment/surgery), the supplied intraocular lens is placed in the patient's eye.

Figure 10:
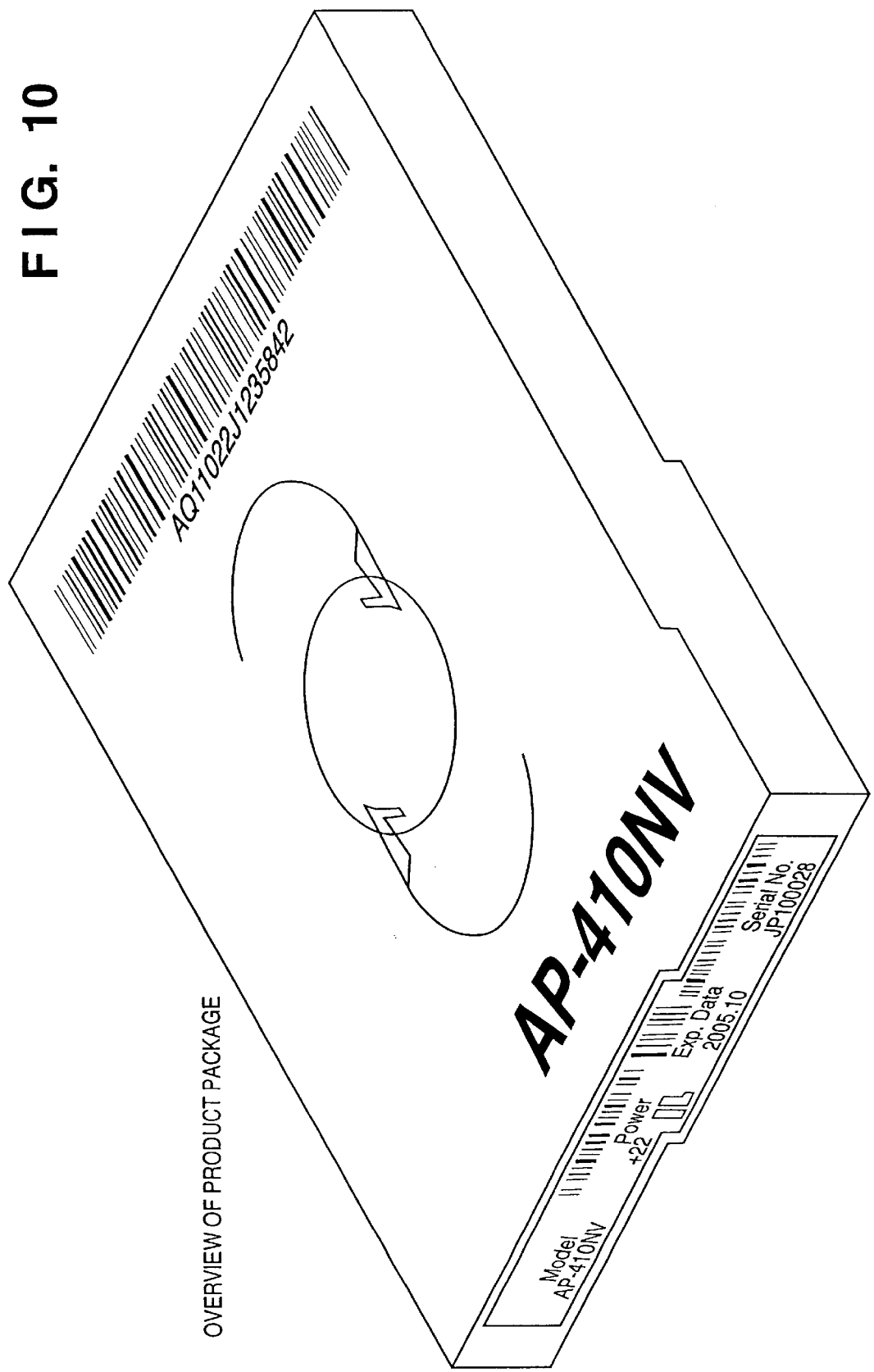
FIG. 10 is an overview of product package of intraocular lens.

The doctor to perform the surgery or assistant finally checks whether or not the intraocular lens is the lens selected for the patient, on the spot, by using a foolproof system. The procedure of the final checking will be described. As shown in FIG. 10, a label on which a product serial code (identification code of numerals or symbols) unique to each delivered product is printed as a bar code, is attached to a product package in which the intraocular lens is encapsulated. The product serial code includes three types of information, a code identifying a model name, a production number (serial number unique to each of products of even the same model), and a lens power. On the label, the model name and the lens power are described in characters so as to be visually checked by the user.

When the package is opened, the doctor or assistant checks the description of the label by visual observation. At the same time, the doctor or assistant reads the bar code on the package by a bar code reader of operation terminal at an operating room. The operation terminal displays the lens model name and the lens power included in the bar code. At the same time, the operation terminal refers to the patient's electronic medical record via the hospital LAN to check whether or not the model and the lens power of the intraocular lens having the product serial code read by the bar code reader correspond with the product information in the electronic record, i.e., the lens model and the lens power of the on-order intraocular lens selected by the doctor. Then the operation terminal informs the doctor/assistant of the correspondence between the data, by a screen image on the display or a message from a speaker. The doctor checks the result of comparison by the display or voice message and then starts the surgery.

By this pre-surgery foolproof system, the probability of human mistake such as use of wrong intraocular lens can be prevented. As a particular example of the operation terminal, a handy terminal with a built-in computer, connected to the hospital LAN with a radio network interface or the like can be used with excellent operability. Further, a laptop PC or desktop PC with a network interface may be employed.

At step 108 (update medical record/selection criterion), the patient data on the electronic medical record is updated. The product serial code read by the bar code reader of the operation terminal upon surgery is automatically recorded into the patient's electronic medical record. At the same time, the product name, the date of use, and the responsible doctor's name (user code) are also automatically recorded in the electronic medical record. After the surgery, if the doctor inputs comment on a usage pattern of the intraocular lens (including quality and claim information) from the above operation terminal or another terminal, the comments are also recorded into the electronic medical record. Further, immediately after or after the surgery, the patient's eye is measured by the various measuring devices for observation of post-surgery status, and the measured data are also recorded in the electronic medical record through the hospital LAN.

Further, a part of the information recorded in the electronic medical record, i.e., a part of the measured data, and information on the product serial code, the date of use, the place of use, the usage pattern and the like of the intraocular lens inserted in the patient's eye are provided to the lens supplier via the Internet. Further, the information on the stock from the hospital stock control system 16, 26 and the company stock control system 35 are recorded in the database of the company stock control system of the lens supplier. Further, after the surgical implantation of the intraocular lens, a form called a patient card is handed to the patient from the hospital. The product serial number is printed on the patient card. If the patient writes personal information, comments on use of the lens, opinions and the like in the patient card and sends it to the lens supplier, the supplier inputs the data from the card and records the data, in relation with the product serial number, into the above-described database.

Further, the lens-selection support service providing system 46 on the lens supplier side recalculates the A constant of the above-described lens power formula (SRK/T formula) based on the received measured data, and automatically updates data in correspondence with the lens type. A particular method of updating is as follows.

Now, it is assumed that a patient is a n-th service user. The measured data of the patient (e.g., naked eye refraction=D0, corrected refraction=D) is transmitted from the hospital. Assuming that the maker's recommended value, the initial A constant is A0, the value of the A constant obtained by using the above values D0 and D is A', and the lens power of the used intraocular lens is P, the A constant is updated as follows. Note that the initial constant A0 is weighted for 1000 patients, however, the value of the constant may be varied.

The n-th A value is updated by:
(1) If $|P| \geq 10$ holds, $|D—D0| \leq 2$: $A=A0 \times (1000+n-1)+A'/(1000+n)$ $|D—D0|>2$: no change
(2) If $10>|P|>5$ holds, $|D—D0| \leq 1$: $A=A0 \times (1000+n-1)+A'/(1000+n)$ $|D—D0|>1$: no change
(3) If $P<5$ holds, $|D—D0| \leq 0.5$: $A=A0 \times (1000+n-1)+A'/(1000+n)$ $|D—D0|>0.5$: no change The updated A constant is a value which reflect the many past A constant values used by all the users of the present service regarding the lens, i.e., the updated constant A means a comprehensive survey of know-how regarding selection of the lens. This A constant is used as the maker's recommended value for the next lens power calculation. That is, the present system is a know-how absorbing type learning system where the A constant optimum of each of various intraocular lenses i.e. selection criterion evolves to more reliable value as the number of times of use and the number of users increase. Further, the doctor can check whether or not his/her know-how is appropriate. This arrangement increases the reliability of the lens selection, and contributes to the homogeneity of selection by reducing variation in selection by respective doctors.

Figure 3:
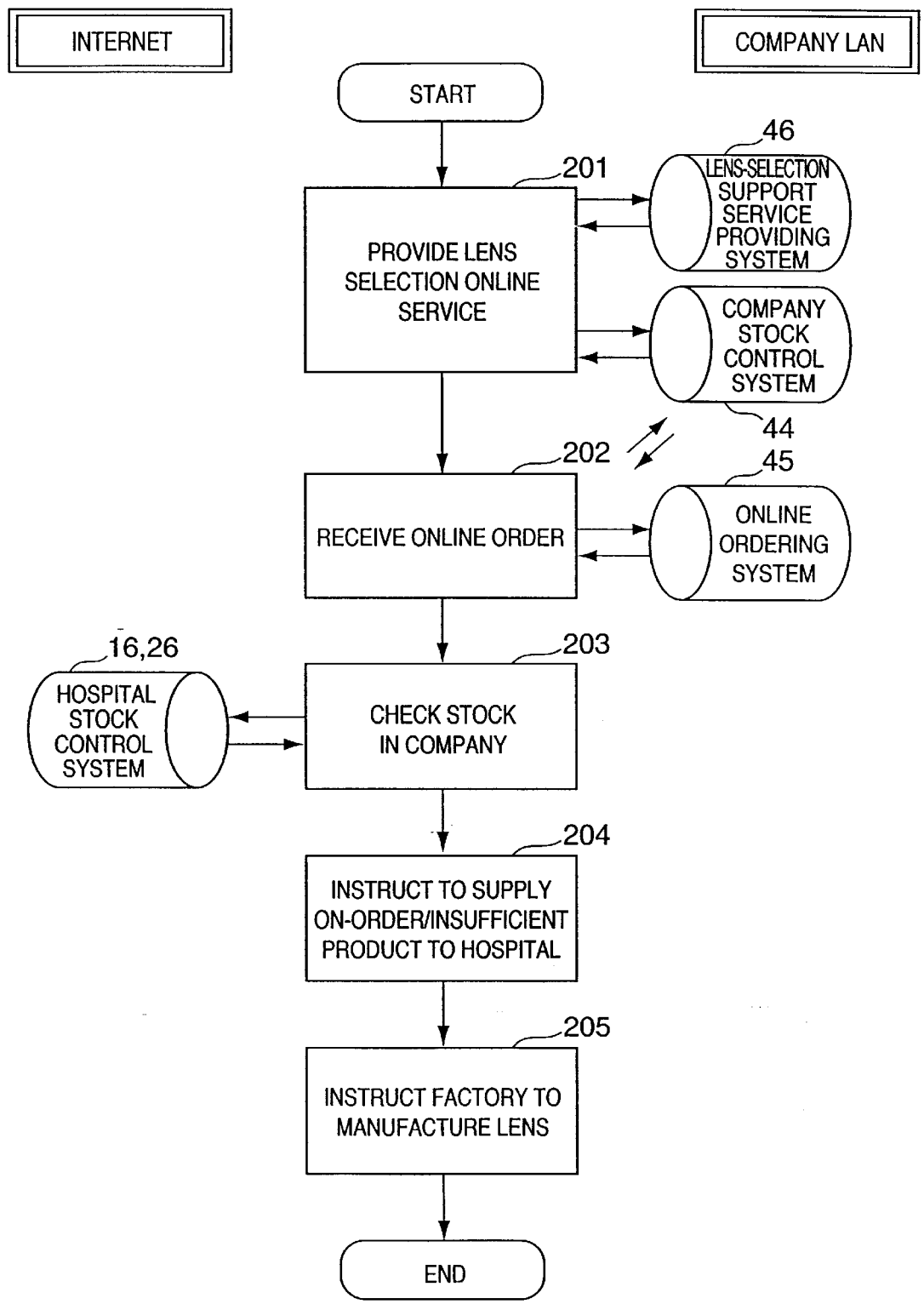
FIG. 3 is a flowchart showing a procedure of service by a provider of medical instrument.

The flow of the service viewed from the medical institution side is as described above. FIG. 3 is a flowchart showing the procedure of lens supply service viewed from the lens supplier side.

At step 201 (provide lens selection online service), the above-described online service is provided through the Internet to the medical institutions such as the hospital A (1), the hospital B (2) and the medical laboratory (3). The lens-selection support service providing system (46) is placed on the server of the company LAN of the lens supplier or the rental server (7). Access to the server via the Internet is permitted from the service utilizing terminal of the respective medical institutions, and the selection of intraocular lens used in the respective medical institutions is supported. Otherwise, as in the case of the hospital B in FIG. 1, a program to provide the service or data may be installed in a local service providing server of the hospital LAN. In this case, the lens selection criterion parameter (A constant) is updated every time the electronic medical record is updated by the hospital after surgery, and the selection criterion becomes more reliable as the number of times of service use increases.

At step 202 (receive online order), an online order from the medical institution is received. The nucleus of the online ordering system to provide the service is constructed in the local servers controlled by the stock control departments of the respective hospitals, while the online ordering system (45) to handle orders from the stock control departments is placed on the server of the company LAN of the lens supplier or the rental server. Further, the online ordering system (45) can access the company stock control system (44) to obtain information on the stock in the company.

The company stock control system (44) performs centralized control on the stocks of all the products handled by the lens supplier. The company stock control system (44) has a database holding various information such as product serial codes (model names and production numbers), dates of production, places of stocks, dates of delivery, dates of use, places of use, usage patterns of all the products manufactured in the factory, and comments from the medical institutions. It can be checked, from the identification code of on-order product, whether or not the on-order product is in stock for delivery by accessing the database. If it is determined that the product is in stock, the online ordering system instructs a computer of the business department or the distribution department to deliver the on-order product to the hospital (step 204). Under the instruction, the business department or the distribution department immediately delivers the on-order product to the hospital.

As the online ordering service is provided in conjunction with the lens-selection support service, the medical institutions can place an order for a selected lens on the spot, thus accurate and quick ordering is realized. Considering a case where a patient is to undertake emergency surgery using an intraocular lens and the lens must be supplied as quick as possible, the level of urgency can be designated upon ordering. In this case, as described below, if the lens is insufficient in stock in the hospital and the maker, the stock of the lens in another medical institution is supplied.

At step 203 (check company stock), it is checked whether or not the on-order intraocular lens is in stock in the company. If the lens is insufficient in stock and the order is urgent, the online ordering system checks stocks outside the company. The system sequentially accesses the stock control systems of medical institutions such as hospitals and laboratories around the orderer hospital, as well as the hospital stock control system of the orderer hospital, via the Internet, to examine whether or not the on-order product is stocked. For this purpose, the lens supplier has previously-assigned limited access right to at least search stock statuses of their products in the stock control systems 16, 26 of the respective medical institutions and the company stock control system 35.

The online ordering system sequentially searches plural positions regarding which the system has access right. Then based on the search results, makes a list of medical institutions having an extra stock of the on-order product, in the order of distance and time, from the closest institution. The system issues an instruction, with the listed results, to the computer of the business department or the distribution department to supply the product (step 204). Under the instruction, the business department or the distribution department dispatches a responsible person to a medical institution that can supply the product most quickly, to deliver the necessary number of products from the extra stock to the orderer hospital. Thus, an order for lens used in an emergency medical treatment can be handled.

Note that at step 203, when the stock control server controlled by the medical institution is accessed from the lens supplier, stocks of other types of intraocular lenses supplied by the supplier in the past are examined. As a result, insufficient or out-of-stock product(s) can be found. The online ordering system first checks the stock of the insufficient product in the company stock control system, and if the product is in stock, instructs the computer of the business department or the distribution department to voluntarily supply the product to the medical institution in which the product is out of stock. If the product is not stocked in the company, the system instructs the factory to manufacture the out-of-stock product (step 205). In this manner, the system is constructed to appropriately supply insufficient/out-of-stock product by utilizing the lens supplier's access partly permitted to the stock control servers of the medical institutions, thereby the medical institutions can always obtain sufficient stocks.

At step 205 (instruct factory to manufacture lens), if the lens is out of stock or a small amount of stock in the supplier and the outside the company, the system instructs a computer of the factory to manufacture the intraocular lens. The factory manufacture the on-order product quickly and ship the product so as to solve the shortage of the stock. Further, the system receives an online order for a customized product for an extraordinary patient's eye in which no standardized lens can be inserted, then the development department designs the customized lens corresponding to the order, and the factory manufactures the lens. In this case, the Internet and the network of the company LAN are utilized and quick manufacturing and supply of the product can be performed. As shown in FIG. 10, each of pre-shipment product packages completed in the factory has a bar code label displaying a unique product serial code. For control of shipped products by bar code, the company stock control system is accessed via the company LAN from the factory computer, and records of new product serial codes are added to the database.

As described above, a part of information recorded in the electronic medical record in the hospital, e.g., a part of measured data, and information on the product serial code, the date of use, the place of use, the usage pattern and the like of the intraocular lens inserted into the patient's eye are provided via the Internet to the lens supplier. Further, the information on the stock status of the product is recorded in the database of the company stock control system of the lens supplier. Further, the information from the patient card is also recorded in the same database. That is, by introduction of the present system, the lens supplier can obtain information of shipped products from the medical institutions and perform follow-up control. As time and place of use of each shipped product can be obtained in correspondence with the product serial code, after-sales support for each product can be easily made. Further, the usage pattern of the product, i.e., information on the quality and claim and the patient's comments and opinions are useful information for improvement of the product. These information are stored in the database of the company stock control system, and accessible from the development department, the manufacturing department and the like via the company LAN. As the useful information can be shared in the company, product development and improvement can be quickly made. Further, the manufacturing technology can be improved.

As described above, according to the present invention, the problem of supply of medical instruments specific to the medical field, that demands cannot be predicted without difficulty and products must be quickly supplied, can be solved. That is, the medical institution can timely receive a medical instrument, and the supplier of medical instrument can efficiently perform delivery and manufacturing control. That is, the introduction of the present invention brings profits to the both medical institution and supplier, and greatly contributes to the development of medical industry.

Further, the present invention provides the selection support service for medical institutions to assist accurate selection of medical instrument regardless of experience or knowledge of the service user.

Further, the electronic medical recording system of the present invention can provide medical services covering details for respective patients by utilizing a communication network. Further, the present invention provides a foolproof system effective upon use of medical instrument to a patient and provides a terminal apparatus to realize the system.

Further, according to the present invention, the supplier of medical instrument can perform follow-up control on shipped products, thus attains timely development and improvement of products and after-sales support.

As many apparently widely different embodiments of the present invention can be made without departing from the spirit and scope thereof, it is to be understood that the invention is not limited to the specific embodiments thereof except as defined in the appended claims.

What is claimed is:

1. A method for providing a selection support service for selecting a medical instrument used in a medical institution by utilizing a network system having a service providing system, a service utilizing terminal of said medical institution and a communication network, comprising:

a step of storing information indicating plural types of medical instruments, in relation with data respectively specific to the medical instruments, into a database of said service providing system;

a step of receiving medical information on a patient held by said medical instrument via said communication network, by said service providing system;

a step of searching said database in accordance with a selection criterion based on the received medical information on said patient, and selecting a medical instrument appropriate to said selection criterion from said plural types of medical instruments, in said service providing system; and a step of displaying information on said selected medical instrument on said service utilizing terminal.

2. The method according to claim 1, further comprising a step of displaying a screen image for inputting medical information on said patient to whom said medical instrument is applied, on said service utilizing terminal.

3. The method according to claim 1, further comprising:

a step of checking a stock status of said selected medical instrument; and a step of displaying information on said medical instrument, with said checked stock status, on said service utilizing terminal.

4. The method according to claim 1, further comprising:

a step of displaying a screen image for receiving an online order for said medical instrument, selected and displayed on said service utilizing terminal, on said service utilizing terminal; and a step of processing the order for said medical instrument received via said communication network.

5. The method according to claim 4, wherein said step of processing the order has a step of instructing to supply said medical instrument to said medical institution.

6. The method according to claim 4, wherein said step of processing the order has a step of instructing a factory to manufacture said medical instrument.

7. The method according to claim 4, wherein said step of processing the order has:

a step of accessing a stock control server controlled by a supplier of said medical instrument to check whether or not said medical instrument is in stock in said supplier; and a step of, if said medical instrument is out of stock in said supplier, accessing a stock control server controlled by an institution other than said medical institution via said communication network to check whether or not said medical instrument is in stock.

8. The method according to claim 1, wherein the medical information on said patient to whom said medical instrument is applied is obtained from said patient's electronic medical record information recorded in an electronic medical recording system controlled by said medical institution.

9. The method according to claim 1, wherein the information on said selected medical instrument is recorded in the electronic medical recording system controlled by said medical institution.

10. The method according to claim 1, further comprising:
a step of obtaining after-use information of said selected medical instrument via said communication network from said medical institution; and
a step of updating said selection criterion based on said after use information.

11. The method according to claim 10, wherein said after-use information on said medical instrument includes measured data after application of said medical instrument to said patient.

12. The method according to claim 1, wherein said database holds data of medical instruments by different makers.

13. The method according to claim 1, wherein said medical instrument is an implanted tool placed in a patient's body.

14. The method according to claim 1, wherein said medical instrument is an intraocular lens, and wherein said information on said patient is ophthalmologic measurement data of said patient, further wherein said selection criterion has a formula to obtain a lens power of intraocular lens based on said ophthalmologic measurement data, further wherein said method further comprising a step of selecting a lens having a lens power satisfying the lens power obtained by said formula from lenses registered in said database.

15. The method according to claim 14, wherein said ophthalmologic measurement data include one or more of corneal power, an axial length, a corneal diameter, a pupil diameter, naked vision, corrected visual acuity, a spherical power upon correction, cylinder and cylinder axis, and wherein said method further comprising a step of searching said database for an intraocular lens satisfying said lens power and other conditions of ophthalmologic measurement data.

16. The method according to claim 14, further comprising a step of updating a coefficient of the formula for obtaining said lens power based on ophthalmologic measurement data after insertion of said intraocular lens into said patient's eye.

17. The method according to claim 1, wherein said communication network is the Internet or a network using a private communication line, and wherein a server of said service providing system is provided on a local area network of said supplier of said medical instrument or on the Internet.

18. The method according to claim 1, wherein a server of said service providing system is provided on a local area network in said medical institution.

19. A system for providing a selection support service for selecting a medical instrument used in a medical institution by utilizing a communication network accessible from a service utilizing terminal of said medical institution, comprising:
a computer system including a database that holds information indicating plural types of medical instruments, in relation with data respectively specific to the medical instruments; and
an interface that connects said computer system to said communication network,
wherein said computer system holds a program for executing:
a step of receiving medical information on a patient held by said medical instrument via said communication network, by said service providing system;
a step of searching said database in accordance with a selection criterion based on the medical information on said patient, and selecting a medical instrument appropriate to said selection criterion from said plural types of medical instruments, in said service providing system; and
a step of displaying information on said selected medical instrument on said service utilizing terminal.

20. The system according to claim 19, wherein said program further executes a step of displaying a screen image for inputting medical information on said patient to whom said medical instrument is applied, on said service utilizing terminal.

21. The system according to claim 19, wherein said program further executes:
a step of checking a stock status of said selected medical instrument; and
a step of displaying information on said medical instrument, with said checked stock status, on said service utilizing terminal.

22. The system according to claim 19, wherein said program further executes:
a step of displaying a screen image for receiving an online order for said medical instrument, selected and displayed on said service utilizing terminal, on said service utilizing terminal; and
a step of processing the order for said medical instrument received via said communication network.

23. The system according to claim 22, wherein said step of processing the order has a step of instructing to supply said medical instrument to said medical institution.

24. The system according to claim 22, wherein said step of processing the order has a step of instructing a factory to manufacture said medical instrument.

25. The system according to claim 22, wherein said step of processing the order has:
a step of accessing a stock control server controlled by a supplier of said medical instrument to check whether or not said medical instrument is in stock in said supplier; and
a step of, if said medical instrument is out of stock in said supplier, accessing a stock control server controlled by an institution other than said medical institution via said communication network to check whether or not said medical instrument is in stock.

26. The system according to claim 19, wherein the medical information on said patient to whom said medical instrument is applied is obtained from said patient's electronic medical record information recorded in an electronic medical recording system controlled by said medical institution.

27. The system according to claim 19, wherein the information on said selected medical instrument is recorded in the electronic medical recording system controlled by said medical institution.

28. The system according to claim 19, wherein said program further executes:
a step of obtaining after-use information of said selected medical instrument via said communication network from said medical institution; and
a step of updating said selection criterion based on after use information.

29. The system according to claim 28, wherein said after-use information on said medical instrument includes measured data after application of said medical instrument to said patient.

30. The system according to claim 19, wherein said database holds data of medical instruments by different makers.

31. The system according to claim 19, wherein said medical instrument is an implanted tool placed in a patient's body.

32. The system according to claim 19, wherein said medical instrument is an intraocular lens, and wherein said information on said patient is ophthalmologic measurement data of said patient, further wherein said selection criterion has a formula to obtain a lens power of intraocular lens based on said ophthalmologic measurement data, further wherein said program further executes a step of selecting a lens having a lens power satisfying the lens power obtained by said formula from lenses registered in said database.

33. The system according to claim 32, wherein said ophthalmologic measurement data include one or more of corneal power, an axial length, a corneal diameter, a pupil diameter, naked vision, corrected visual acuity, a spherical power upon correction, cylinder and cylinder axis, and wherein said program further executes a step of searching said database for an intraocular lens satisfying said lens power and other conditions of ophthalmologic measurement data.

34. The system according to claim 32, wherein said program further executes a step of updating a coefficient of the formula for obtaining said lens power based on ophthalmologic measurement data after insertion of said intraocular lens into said patient's eye.

35. The system according to claim 19, wherein said communication network is the Internet or a network using a private communication line, and wherein a server of said service providing system is provided on a local area network of said supplier of said medical instrument or on the Internet.

36. The system according to claim 19, wherein a server of said service providing system is provided on a local area network in said medical institution.

37. A method for providing a selection support service for selecting a medical instrument used in a medical institution by utilizing a network system having a service providing system, a service utilizing terminal of said medical institution and a communication network, comprising:

a step of storing information indicating plural types of medical instruments, in relation with data respectively specific to the medical instruments, into a database of said service providing system;

a step of receiving medical information on a patient held by said medical instrument via said communication network, by said service providing system;

a step of searching said database in accordance with a selection criterion based on the received medical information on said patient, and selecting a medical instrument appropriate to said selection criterion from said plural types of medical instruments, in said service providing system;

a step of obtaining measured data of said patient after application of said medical instrument to said patient via said communication network; and a step of updating said selection criterion based on said information.

38. The method according to claim 37, wherein said medical instrument is an implanted tool placed in a patient's body.

39. The method according to claim 37, wherein said medical instrument is an intraocular lens, and wherein said information on said patient is ophthalmologic measurement data of said patient, further wherein said selection criterion has a formula to obtain a lens power of intraocular lens based on said ophthalmologic measurement data, further wherein said method further comprises a step of selecting a lens having a lens power satisfying the lens power obtained by said formula from lenses registered in said database.

40. The method according to claim 39, wherein said ophthalmologic measurement data include one or more of corneal power, an axial length, a corneal diameter, a pupil diameter, naked vision, corrected visual acuity, aspherical power upon correction, cylinder and cylinder axis, and wherein said method further comprises a step of searching said database for an intraocular lens satisfying said lens power and other conditions of ophthalmologic measurement data.

41. The method according to claim 39, further comprising a step of updating a coefficient of the formula for obtaining said lens power based on ophthalmologic measurement data after insertion of said intraocular lens into said patient's eye.

42. The method according to claim 37, wherein said communication network is the Internet or a network using a private communication line, and wherein a server of said service providing system is provided on a local area network of said supplier of said medical instrument or on the Internet.

43. The method according to claim 37, wherein a server of said service providing system is provided on a local area network in said medical institution.

* * * * *

UNITED STATES PATENT AND TRADEMARK OFFICE
CERTIFICATE OF CORRECTION

PATENT NO. : 6,801,913 B2
DATED : October 5, 2004
INVENTOR(S) : Isao Matsumura et al.

It is certified that error appears in the above-identified patent and that said Letters Patent is hereby corrected as shown below:

<u>Title page,</u>
Item [57], ABSTRACT,
Line 1, "instrument," should read -- institution, --.

<u>Column 1,</u>
Line 47, "emergent" should read -- emergency --; and
Line 59, "situations." should read -- situation. --.

<u>Column 2,</u>
Line 15, "makers" should read -- makers, --;
Line 40, "place" should read -- places --; and
Line 50, "has its" should read -- has as its --.

<u>Column 5,</u>
Line 63, "service" should read -- service, --;
Line 64, "(, and" should read -- and --; and "necessary,)" should read -- necessary, --.

<u>Column 66,</u>
Line 66, "a" (second occurrence) should be deleted; and
Line 67, "spherical" should read -- aspherical --.

<u>Column 7,</u>
Line 25, "bellow." should read -- below. --.

<u>Column 8,</u>
Line 3, "specification" should read -- specifications --;
Lines 6 and 15, "1 maker" should read -- one maker --; and
Line 47, "4 input" should read -- four input --.

<u>Column 11,</u>
Line 8, "reflect" should read -- reflects --.

<u>Column 12,</u>
Line 62, "stock in" should read -- stock is in --;
Line 65, "manufacture" should read -- manufactures --; and "ship" should read -- ships --.

<u>Column 13,</u>
Line 32, "information" should read -- informations --; and
Line 61, "attains" should read -- attaining --.

UNITED STATES PATENT AND TRADEMARK OFFICE
CERTIFICATE OF CORRECTION

PATENT NO. : 6,801,913 B2
DATED : October 5, 2004
INVENTOR(S) : Isao Matsumura et al.

It is certified that error appears in the above-identified patent and that said Letters Patent is hereby corrected as shown below:

Column 14,
Line 12, "instrument" should read -- institution --.

Column 15,
Line 6, "after use" should read -- after-use --;
Line 21, "of intraocular" should read -- of an intraocular --;
Lines 23 and 31, "comprising" should read -- comprises --;
Line 29, "a spherical" should read -- aspherical --; and
Line 62, "instrument" should read -- institution --.

Column 16,
Line 56, "after use" should read -- after-use --.

Column 17,
Line 5, "of intraocular" should read -- of an intraocular --;
Line 13, "a spherical" should read -- aspherical --; and
Line 42, "instrument" should read -- institution --.

Column 18,
Line 18, "of intraocular" should read -- of an intraocular --.

Signed and Sealed this

Tenth Day of January, 2006

JON W. DUDAS
*Director of the United States Patent and Trademark Office*